United States Patent
Melsa et al.

(10) Patent No.: US 10,259,805 B2
(45) Date of Patent: Apr. 16, 2019

(54) PROCESS FOR MAKING CRYSTALLINE FORM A OF GEFITINIB

(71) Applicant: Synthon B.V., Nijmegen (NL)

(72) Inventors: Petr Melsa, Blansko (CZ); Radomir Skoumal, Blansko (CZ)

(73) Assignee: Synthon B.V., Nijmegen (NL)

( * ) Notice: Subject to any disclaimer, the term of this patent is extended or adjusted under 35 U.S.C. 154(b) by 0 days.

(21) Appl. No.: 16/067,330

(22) PCT Filed: Dec. 22, 2016

(86) PCT No.: PCT/EP2016/082322
§ 371 (c)(1),
(2) Date: Jun. 29, 2018

(87) PCT Pub. No.: WO2017/114735
PCT Pub. Date: Jul. 6, 2017

(65) Prior Publication Data
US 2019/0010147 A1 Jan. 10, 2019

(30) Foreign Application Priority Data
Dec. 30, 2015 (EP) .................................. 15203106

(51) Int. Cl.
*C07D 413/12* (2006.01)
*C07D 239/94* (2006.01)

(52) U.S. Cl.
CPC ......... *C07D 413/12* (2013.01); *C07D 239/94* (2013.01); *C07B 2200/13* (2013.01)

(58) Field of Classification Search
CPC .................................................. C07D 413/12
See application file for complete search history.

(56) References Cited

U.S. PATENT DOCUMENTS

| | | | | |
|---|---|---|---|---|
| 7,612,077 B2 * | 11/2009 | Gilday | ................... | A61K 9/284 514/258.1 |
| 8,198,281 B2 * | 6/2012 | Kawasaki | ............ | C07D 487/04 514/252.16 |
| 2018/0298019 A1 * | 10/2018 | Liu | ...................... | A61K 31/517 |

FOREIGN PATENT DOCUMENTS

| | | | |
|---|---|---|---|
| CN | 101 973 944 A | | 2/2011 |
| CN | 101973944 A | * | 2/2011 |
| CN | 103102316 | | 1/2013 |
| CN | 103030599 A | * | 4/2013 |
| CN | 103102316 A | * | 5/2013 |
| CN | 103319422 A | * | 9/2013 |
| CN | 103360326 A | * | 10/2013 |
| CN | 103896862 A | * | 7/2014 |
| CN | 103896863 A | * | 7/2014 |
| CN | 103910690 A | * | 7/2014 |
| CN | 104277005 A | * | 1/2015 |
| CN | 104693127 A | * | 6/2015 |
| CN | 105294715 A | * | 2/2016 |
| CN | 106083739 A | * | 11/2016 |
| EP | 566226 | | 10/1993 |
| EP | 1480650 A1 | * | 12/2004 ............. A61K 9/284 |
| RU | 2577518 C2 | * | 3/2016 |
| WO | WO 96/33980 | | 10/1996 |
| WO | WO 03/072108 | | 9/2003 |
| WO | WO-03072108 A1 | * | 9/2003 ............. A61K 9/284 |
| WO | WO 2006/090413 A1 | | 8/2006 |
| WO | WO-2006090413 A1 | * | 8/2006 ........... C07D 239/94 |
| WO | WO-2014208954 A1 | * | 12/2014 ........... C07D 239/94 |
| WO | WO-2015170345 A1 | * | 11/2015 ........... A61K 31/517 |
| WO | WO-2017083788 A1 | * | 5/2017 ........... A61K 9/0053 |

OTHER PUBLICATIONS

English-Language Machine Translation of CN 103102316 (2013) (Year: 2013).*
S. Thorat et al., CrystEngComm (2014) (Year: 2014).*
Solid State Characterization of Pharmaceuticals (R.A. Storey et al., eds., 2011) (Year: 2011).*
G. Liu et al., Journal of $CO_2$ Utilization (2017) (Year: 2017).*
English-Language Machine Translation of WO 2014/208954 (2014) (Year: 2014).*
English-Language Machine Translation of CN 103910690 (2014) (Year: 2014).*
English-Language Machine Translation of CN 103896862 (2014) (Year: 2014).*
English-Language Machine Translation of CN 104693127 (2015) (Year: 2015).*
English-Language Machine Translation of CN 103896863 (2014) (Year: 2014).*
English-Language Machine Translation of CN 103360326 (2013) (Year: 2013).*
English-Language Machine Translation of CN 103319422 (2013) (Year: 2013).*

(Continued)

*Primary Examiner* — Alexander R Pagano
(74) *Attorney, Agent, or Firm* — Buscher Patent PLLC

(57) ABSTRACT

The present invention relates to a process for preparation of crystalline Form 1 of gefitinib of formula (1) characterized by a XRPD powder diffraction pattern comprising, inter alia, peaks at about 7.14, 11.26, 14.25, 15.86, 24.33 and 26.40 degrees 2 theta (±0.2 degrees 2 theta), the process comprising the steps: 1. Dissolving gefitinib in a solvent mixture comprising water and an alcohol selected form ethanol and butanol, wherein the ratio between water and alcohol is between 1:16 and 1:25 (vol:vol) 2. Isolating gefitinib Form 1.

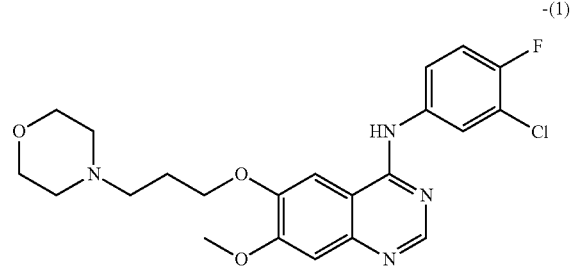

-(1)

11 Claims, 1 Drawing Sheet

(56) References Cited

OTHER PUBLICATIONS

English-Language Machine Translation of CN 104277005 (2015) (Year: 2015).*
English-Language Machine Translation of CN 101973944 (2011) (Year: 2011).*
English-Language Machine Translation of CN 103030599 (2013) (Year: 2013).*

* cited by examiner

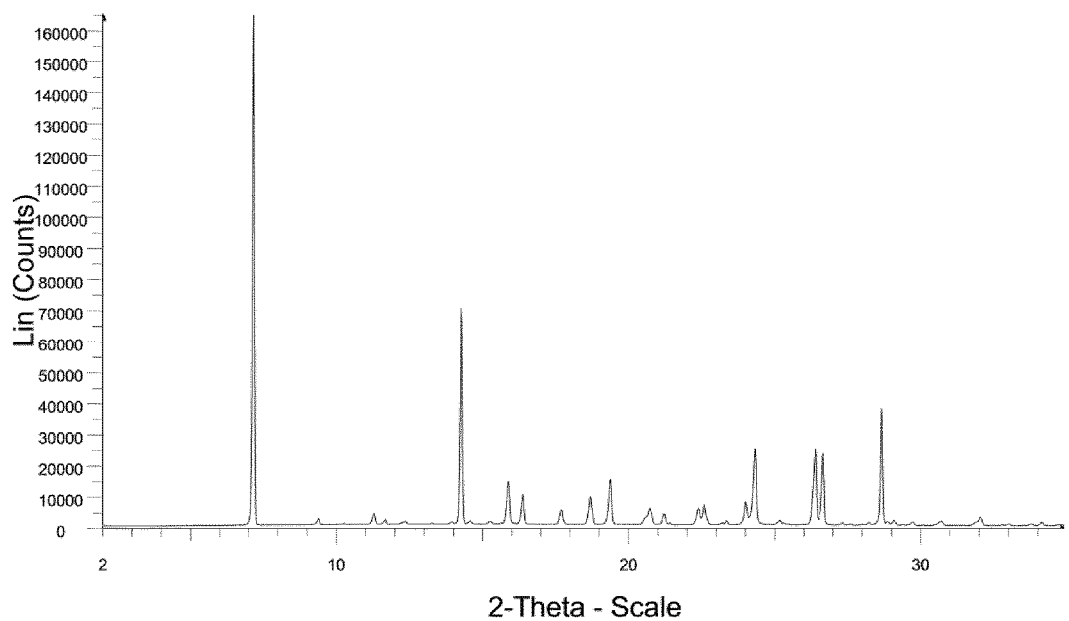

PROCESS FOR MAKING CRYSTALLINE FORM A OF GEFITINIB

BACKGROUND OF THE INVENTION

The present invention relates to an improved process for making gefitinib crystalline Form 1.

Gefitinib, chemically 4-(3-chloro-4-fluorophenylamino)-7-methoxy-6-[3-(4-morpholinyl)propoxy] quinazoline of formula (1),

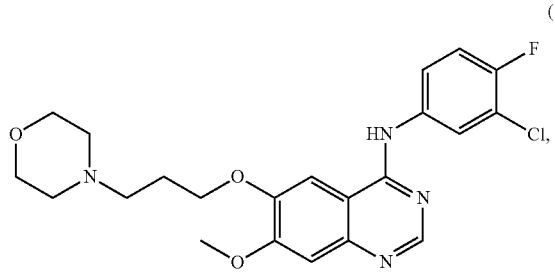

(1)

is a pharmaceutically active compound acting as a selective inhibitor of epidermal growth factor receptor's (EGFR) tyrosine kinase. Gefitinib is used as a medicament for the treatment of e.g., locally advanced or metastatic non-small-cell lung cancer (NSCLC), and is available, e.g., under the brand name Iressa®, as gefitinib 250 mg tablets for oral administration.

Gefitinib was generically disclosed in EP566226. Specifically, gefitinib and its salts were disclosed in EP 823900, whereas different polymorphic forms of gefitinib base were disclosed in EP1480650 (Form 1, anhydrate and Form 5, trihydrate) and WO2006/090413 (Form 6, monohydrate).

Among the solid state forms of gefitinib, the crystalline Form 1 of EP1480650 is particularly preferred in the pharmaceutical industry as it is sufficiently stable and non-hygroscopic with a good processability and compatibility with pharmaceutical excipients for making solid state dosage forms.

Processes for preparation of gefitinib Form 1 have been disclosed in several prior art documents for example in CN103102316 or CN101973944. The drawback of the processes is a use of high volumes of solvents due to low solubility of gefitinib.

BRIEF DESCRIPTION OF THE INVENTION

The present invention relates to a straightforward process for making crystalline gefitinib Form 1, as defined hereinafter, which is effective in a reliable production environment on an industrial scale without the need of using high volumes of solvents for dissolving gefitinib.

The first object of this invention is a process for preparation of crystalline Form 1 of gefitinib of formula (1) characterized by a XRPD powder diffraction pattern comprising, inter alia, peaks at about 7.14, 11.26, 14.25, 15.86, 24.33 and 26.40 degrees 2 theta (+0.2 degrees 2 theta),

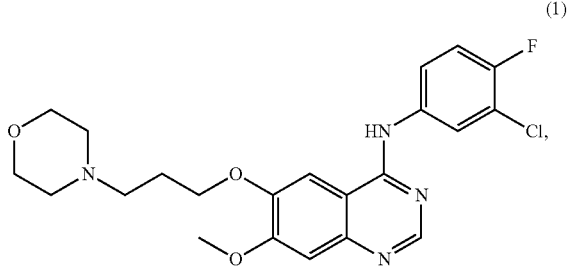 [SMILES: COc1cc2ncnc(Nc3ccc(F)c(Cl)c3)c2cc1OCCCN1CCOCC1]

(1)

the process comprising the steps:
1. Dissolving gefitinib in a solvent mixture comprising water and an alcohol selected form ethanol and butanol, wherein the ratio between water and alcohol is between 1:16 and 1:25 (vol:vol);
2. Isolating gefitinib Form 1.

BRIEF DESCRIPTION OF THE DRAWINGS

The sole FIGURE depicts the X-Ray Powder Diffractogram (XRPD) of Form 1 of gefitinib obtained by the process of Example 2.

DETAILED DESCRIPTION OF THE INVENTION

The present invention relates to a process for making crystalline Form 1 of gefitinib. Throughout the disclosure and claims, the "Form 1" of gefitinib is a crystalline form characterized by a XRPD powder diffraction pattern comprising, inter alia, peaks at about 7.14, 11.26, 14.25, 15.86, 24.33 and 26.40 degrees 2 theta (+0.2 degrees 2 theta) obtained when measured with CuKα1 radiation ($\lambda$=1.54060 Å). The XRPD pattern of gefitinib Form 1 obtainable by the process of the present invention substantially corresponds to that disclosed for gefitinib Form 1 in EP1480650. "Substantially corresponds" is meant to cover variations/differences in the pattern that would not be understood by a worker skilled in the art to represent a difference in crystal structure, but rather differences in technique and sample preparation.

The Form 1 of gefitinib produced by the process of the present invention has an excellent batch-to-batch uniformity in the size and shape of the formed crystals. According to one particular aspect of the invention, the gefitinib Form 1 crystals produced by the process of the present invention are preferably substantially free from other crystalline forms of gefitinib. In this respect, the "substantially free" means that less than 10%, and more preferably less than 5% of other crystalline forms are present in the precipitated and/or isolated product comprising the Form 1 of gefitinib.

The starting material for the process of the invention, gefitinib, is either commercially available or may be produced according to known procedures, e.g. according to that disclosed in WO96/33980.

The object is a process for preparation of crystalline Form 1 of gefitinib of formula (1) characterized by a XRPD powder diffraction pattern comprising, inter alia, peaks at about 7.14, 11.26, 14.25, 15.86, 24.33 and 26.40 degrees 2 theta (+0.2 degrees 2 theta),

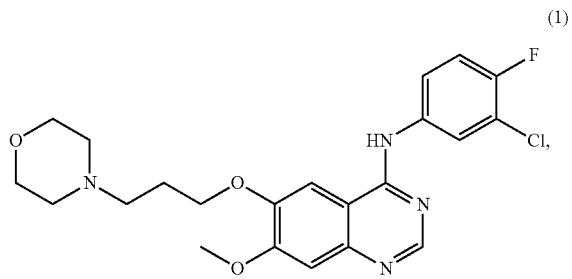 [SMILES: COc1cc2ncnc(Nc3ccc(F)c(Cl)c3)c2cc1OCCCN1CCOCC1]

the process comprising the steps:
1. Dissolving gefitinib in a solvent mixture comprising water and an alcohol selected form ethanol and butanol, wherein the ratio between water and alcohol is between 1:16 and 1:25 (vol:vol);
2. Isolating of gefitinib Form 1.

In the first step of the process of the present invention, the compound of formula (1) is combined, typically under stirring, with a solvent mixture comprising water and an alcohol selected from C1-C6 aliphatic alcohol, preferably ethanol or butanol. Butanol might be either 1-butanol or 2-butanol or a mixture thereof. The ratio between water and an alcohol is between 1:16 and 1:25 (vol:vol), preferably between 1:18 and 1:20 (vol:vol), the most preferred ratio is 1:20 (vol:vol). Solvent mixtures with higher water content show presence of different polymorphs from polymorph 1 (for example hydrated forms of gefitinib) in the isolated gefitinib. The mixture of solvents and gefitinib can be heated, for example to the reflux temperature of the mixture, to dissolve gefitinib in the solvent mixture. After dissolving of the gefitinib in the mixture, the mixture can be cooled to a temperature between 50-75° C., preferably at 75° C. The mixture is then preferably seeded with gefitinib Form 1 particles. The mixture can be further cooled at a temperature between −10° C. and the room temperature (20-25° C.), preferably at the room temperature. The mixture is stirred at this temperature for 5-20 hours, preferably for 10-16 hours wherein the crystalline gefitinib Form 1 precipitates from the mixture.

The solvent mixture comprising water and an alcohol selected from ethanol or butanol and their ratio are essential for the presented invention. Gefitib Form 1 can be precipitate from the mixture by any technique, e.g. crystallization, evaporation of the solvents etc.

The precipitated product can be isolated from the mixture by conventional techniques, e.g. filtering or centrifugation, and can be washed and dried.

Using the disclosed process the amount of solvent(s) used for crystallization of gefitinib Form 1 can be surprisingly decreased comparing to the prior art processes.

The gefitinib Form 1 prepared by the process of the present invention can be formulated and used in pharmaceutical compositions. For instance, a suitable pharmaceutical composition may comprise gefitinib Form 1 and at least one pharmaceutically acceptable excipient.

The gefitinib Form 1 prepared by the process of the present invention is suitable for the treatment of a wide range of conditions including e.g., locally advanced or metastatic non-small-cell lung cancer (NSCLC). The invention will be further described with reference to the following non-limiting examples.

EXAMPLES

Example 1

A suspension of gefitinib (10 g, 22.29 mmol) in 2-butanol (85.3 ml) and water (4.7 ml) was heated to 94° C. (reflux) with stirring to obtain a clear solution. The solution was cooled to 75° C. with stirring. It was seeded with gefitinib Form 1 and a resulting suspension was stirred at 75° C. for 1 hour. Then it was cooled to 23° C. over 2 hours, stirred for additional 12 hours, filtered, washed with 2-butanol (10 ml) and dried to afford Gefitinib Form 1 in 87% yield.

Example 2

A suspension of gefitinib (10 g, 22.29 mmol) in 2-butanol (88 ml) and water (4.4 ml) was heated to 94° C. (reflux) with stirring to obtain a clear solution. The solution was cooled to 75° C. with stirring. It was seeded with gefitinib Form 1 and a resulting suspension was stirred at 75° C. for 1 hour. Then it was cooled to 23° C. over 2 hours, stirred for additional 12 hours, filtered, washed with 2-butanol (10 ml) and dried to afford Gefitinib Form 1 in 85% yield.

Example 3

A suspension of gefitinib (10 g, 22.29 mmol) in ethanol (88 ml) and water (4.4 ml) was heated to reflux with stirring to obtain a clear solution. The solution was cooled to 75° C. with stirring. It was seeded with gefitinib Form 1 and a resulting suspension was stirred at 75° C. for 1 hour. Then it was cooled to 23° C. over 2 hours, stirred for additional 13 hours, filtered, washed with ethanol (10 ml) and dried to afford Gefitinib Form 1 in 86% yield.

An XRPD (Presented in FIG. 1) that corresponds to gefitinib Form 1 was then obtained using the following measurement conditions:

Bruker-AXS D8 Vario diffractometer with 0/2θ geometry (reflection mode), equipped with a Vantec PSD detector

| | |
|---|---|
| Start angle (2θ): | 2.0° |
| End angle (2θ): | 35.0° |
| Scan step width: | 0.02° |
| Scan step time: | between 0.2-2.0 seconds |
| Radiation type: | Cu |
| Radiation wavelengths: | 1.5406 Å (Kα1), primary monochromator used |
| Exit slit: | 6.0 mm |
| Focus slit: | 0.2 mm |
| Divergence slit: | Variable (V20) |
| Antiscatter slit: | 11.8 mm |
| Receiving slit: | 20.7 mm |

The invention claimed is:
1. A process for making crystalline gefitinib Form 1 of formula (1),

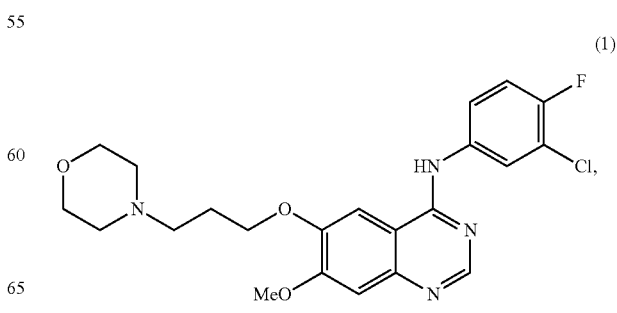

comprising the steps:
dissolving gefitinib in a solvent mixture comprising water and an alcohol selected from ethanol and butanol, wherein the ratio between water and alcohol is between 1:16 and 1:25 (vol:vol);
precipitating crystalline gefitinib Form 1 from said solvent mixture; and
isolating gefitinib Form 1.

2. The process according to claim 1, wherein the ratio between water and the alcohol is between 1:18 and 1:20 (vol:vol).

3. The process according to claim 1 wherein the ratio is 1:20 (vol:vol).

4. The process according to any of claim 1, wherein the concentration of gefitinib in the mixture is between 0.08 g/ml and 0.15 g/ml.

5. The process according to claim 1, wherein said precipitating step comprises cooling said solvent mixture.

6. The process according to claim 5, wherein said dissolving step comprises heating said solvent mixture.

7. The process according to claim 6, wherein said precipitating step further comprises seeding said solvent mixture with gefitinib Form 1 particles.

8. The process according to claim 7, wherein said cooling of said solvent mixture comprises cooling to a temperature within the range of 50-75° C. and after said seeding with gefitinib Form 1 particles, further cooling said solvent mixture to a temperature within the range of −10° C. to 25° C.

9. The process according to claim 8, wherein the concentration of gefitinib in the solvent mixture is between 0.08 g/ml and 0.15 g/ml.

10. The process according to claim 1, wherein said isolating step comprises filtering said solvent mixture to obtain said crystalline gefitinib Form 1.

11. The process according to claim 10, wherein said isolating step further comprises washing and drying said obtained crystalline gefitinib Form 1.

\* \* \* \* \*